Figure 1:
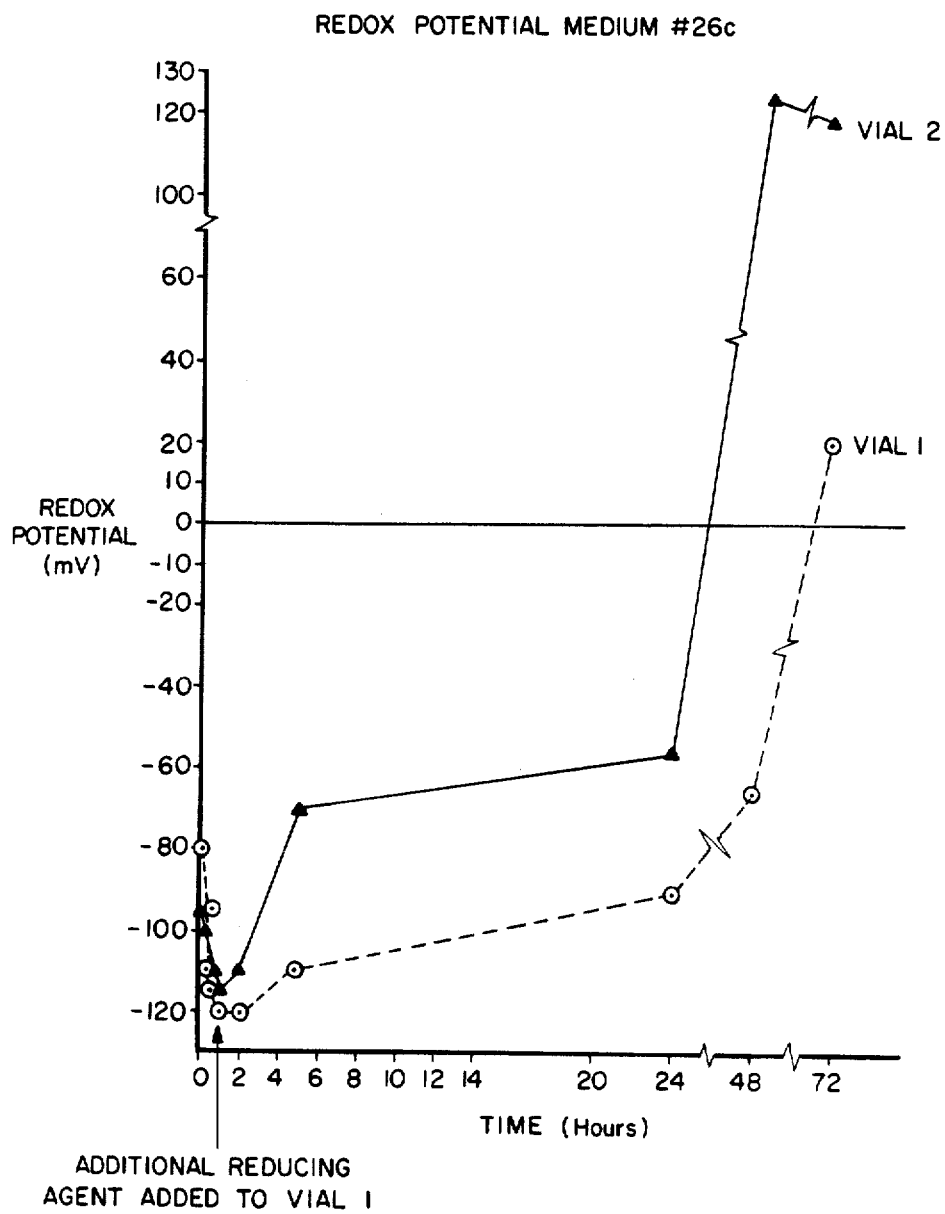

United States Patent [19]

Bryan

[11] Patent Number: 4,529,702

[45] Date of Patent: Jul. 16, 1985

[54] TRANSPORT MEDIUM FOR MICRO-ORGANISMS

[75] Inventor: Lawrence E. Bryan, Calgary, Canada

[73] Assignee: Her Majesty the Queen in right of Canada, as represented by the Minister of National Defence, Ottawa, Canada

[21] Appl. No.: 479,916

[22] Filed: Mar. 28, 1983

[51] Int. Cl.³ .......................... C12N 1/20; C12N 1/04
[52] U.S. Cl. ..................................... 435/253; 435/260
[58] Field of Search ....................... 435/253, 260, 243

[56] References Cited

PUBLICATIONS

Shibata et al., Chem. Abst. vol. 98 (1983), p. 157,588u.

*Primary Examiner*—Sam Rosen
*Attorney, Agent, or Firm*—Cushman, Darby & Cushman

[57] ABSTRACT

The invention disclosed is an improved transport medium for microorganisms, the improvement residing in the inclusion of $Mg^{++}$ in a concentration of 0.6 to 1.2 g per liter of medium, preferably about 1.0 g/l. Further improvement resides in the timing of inclusion of the reducing agent, sodium thioglycollate, i.e. just before use. It has also been found that the detoxification agent, activated charcoal, may be included in concentrations of 5–10 g/l of medium.

10 Claims, 7 Drawing Figures

N. MENINGITIDIS — EFFECT OF TIME OF ADDITION OF REDUCING AGENT

N. GONORRHOEAE  EFFECT OF TIME OF ADDITION OF REDUCING AGENT

H INFLUENZAE    EFFECT OF VARYING CHARCOAL CONCENTRATION

TRANSPORT MEDIUM FOR MICRO-ORGANISMS

This invention relates to a transport medium for micro-organisms and in particular to a universal transport medium for supporting the viability of a wide spectrum of micro-organisms during transport from the field to a remote laboratory for testing.

Various transport media are known in the art. Many of these media are agar based. Over the years, various substances have been added to the agar base to alter its growth potential. For example, the transport medium described in Canadian Pat. No. 976,492 which issued Oct. 21, 1975 to John E. Martin et al is specifically for *N. gonorrhoeae* and *N. meningitidis*. The medium disclosed comprises 2.0-2.5 percent agar, 0.25 percent dextrose and an effective amount of diamino benzyl pyrimidine to screen out Proteus.

A widely used transport medium is known in the art as Modified Stuart Transport Medium. This medium is described in the literature in C. R. Amies: Canad. J. Public Health, July 1967, Vol. 58; 296.

The composition of the Modified Stuart Medium is as follows

| TRANSPORT MEDIUM, NEW FORMULA | |
|---|---|
| Water, distilled | 1000 ml. |
| Agar | 4.0 g. |
| Heat until dissolved, then add, while hot: | |
| NaCl | 3.0 g. |
| KCl | 0.2 g. |
| $Na_2HPO_4$ anhydrous | 1.15 g. |
| (or $Na_2HPO_4.12H_2O$) | 2.9 g. |
| $KH_2PO_4$ | 0.2 g. |
| Sodium thioglycollate | 1.0 g. |
| (= Mercapto-acetic acid, sodium salt) | |
| $CaCl_2$, 1.0% solution, freshly prepared | 10.0 ml. |
| $MgCl_2.6H_2O$, 1.0% solution | 10.0 ml. |
| Stir until dissolved | 10.0 g. |
| Charcoal, Pharmaceutical neutral | |

Distribute into 6.0 ml screw-cap bottles of vials, stirring meanwhile to keep the charcoal evenly suspended. Screw down the caps firmly. Autoclave at 15 lb. for 20 minutes. Invert the bottles just before the medium sets in order to distribute the charcoal uniformly. Re-tighten caps if necessary. Store in a cool place. The final pH is 7.2-7.4.

The composition is sold under the trademark Culturette by Marion Scientific Corporation of Kansas City, Mo.

According to the invention, a transport medium for micro-organisms is contemplated, essentially comprising a composition of 3-4 g agar and 0.6 to 1.2 g, preferably, about 1.0 g, of $Mg^{++}$ per liter of transport medium.

The problem was approached by examining a large number of different factors which were known to alter the viability of various micro-organisms. These included attempts to stabilize membrane integrity, maintenance of a reduced environment to prevent oxidative activity of a variety of materials in medium and specimens, control of ionic composition of the medium to mimic intracellular ionic concentrations and to best support viability, to assess variations of osmolarity to determine maximum viability, to assess the need for carbon and nitrogen sources and to assess the need for and the type of detoxification agents for a variety of materials.

A larger number of different formulations were examined to assess viability of a variety of bacteria, a virus, a mycoplasma and a Chlamydial organism. The most effective formulations were selected for more extensive testing.

Figure 2A:
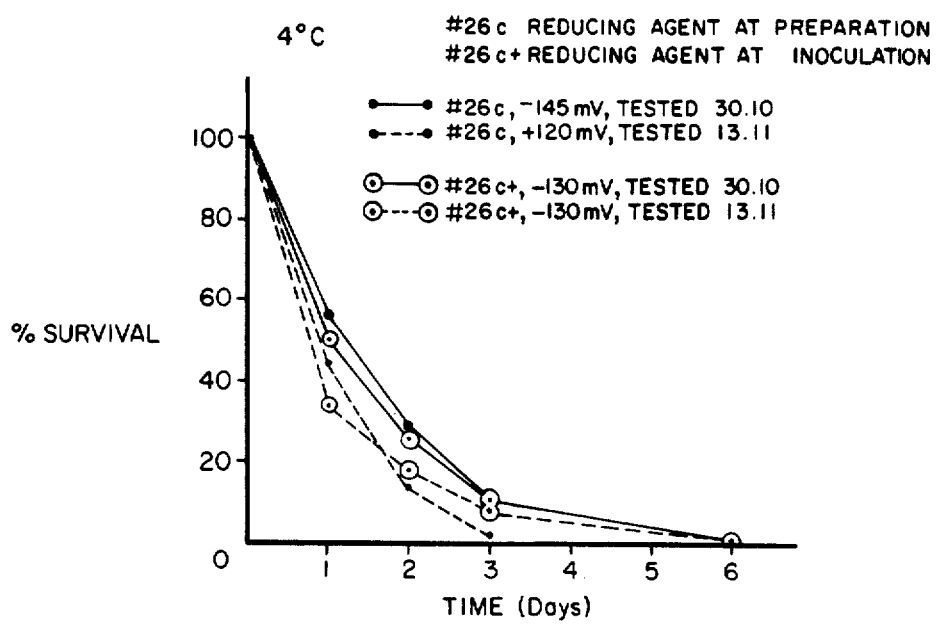
Figure 2B:
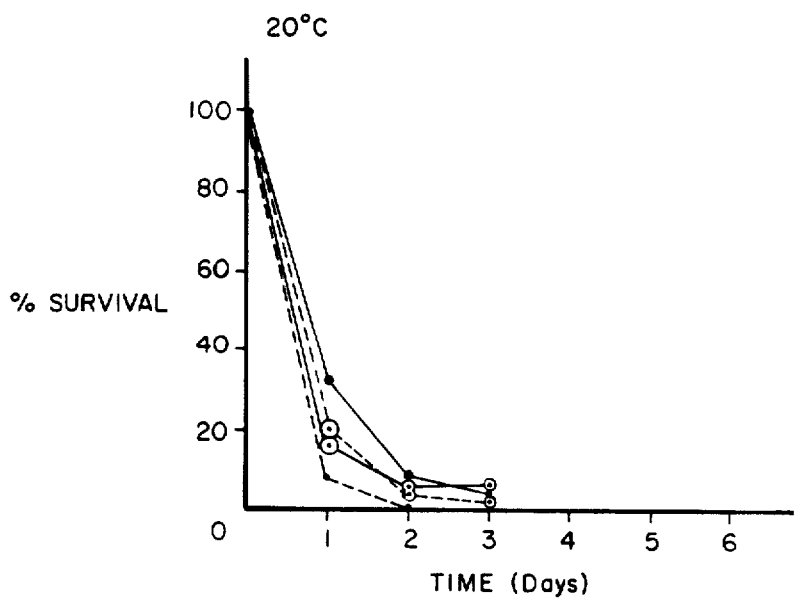
Figure 3A:
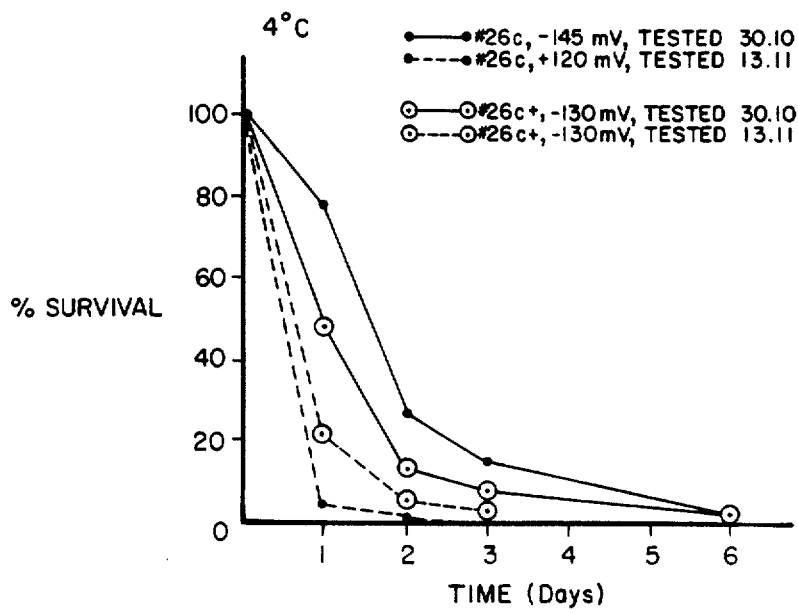
Figure 3B:
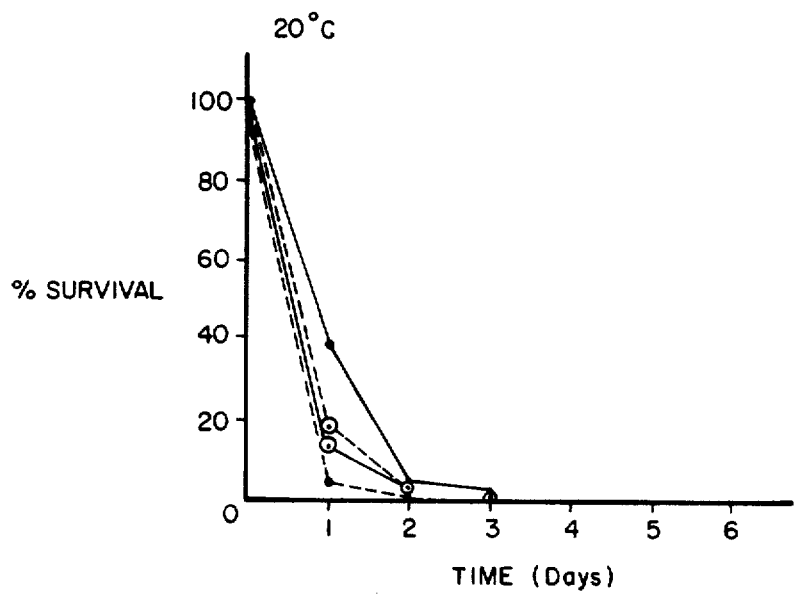
Figure 4A:
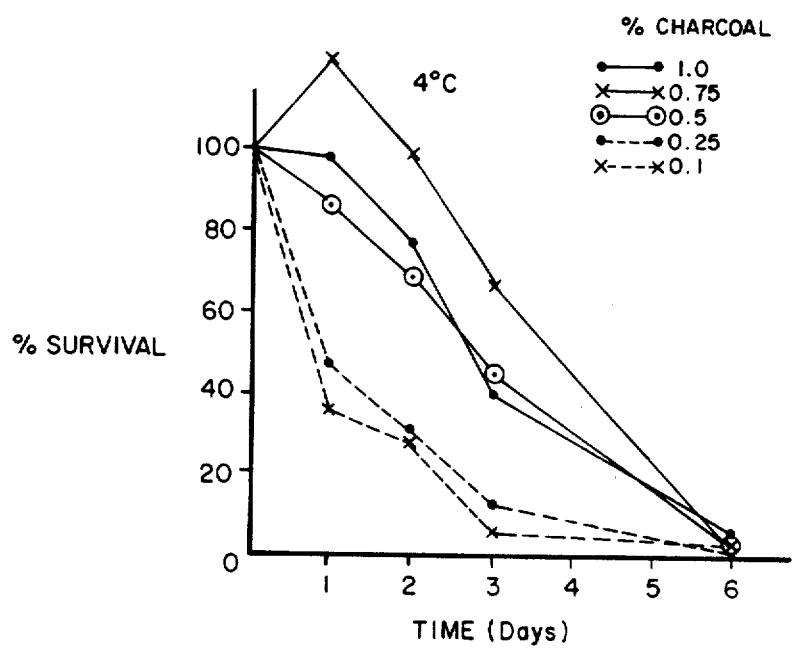
Figure 4B:
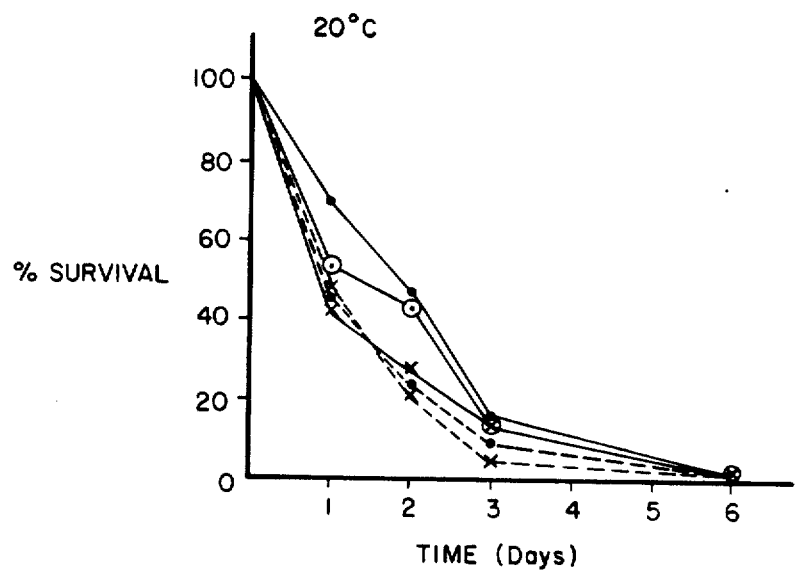

In the drawing which illustrates the preferred embodiment of the invention,

FIGS. 1 to 3 are graphs which illustrate the re-dox potential of the medium following the addition of reducing agent, and FIG. 4 is a graph which illustrates the effect of varying the concentration of the detoxification agent (charcoal).

A promising formulation identified herein as medium No. 6 was developed by modifying the Amies transport medium discussed above. The modifications include increasing the concentration of magnesium, sodium and potassium ions.

The specific formulation No. 6 is as follows:

| The specific formulation No. 6 is as follows: | |
|---|---|
| Distilled water | 1000 mls |
| Agar (purified) | 3 gms |
| Heat until dissolved and add while hot | |
| NaCl | 10 gm |
| KCl | .2 g |
| Stir until dissolved and add | |
| $K_2HPO_4$ | 1.39 g |
| $KH_2PO_4$ | .2 g |
| Stir until dissolved and add | |
| (Starch if being used, 1 g in 10 mls in water) | |
| Add very gradually while stirring | |
| $CaCl_2.2H_2O$ 1% solution | 10 ml |
| $MgCl_2.6H_2O$ 1% solution | 20 mls |
| Na Thioglycollate | 1.0 g |
| Activated Charcoal | 10.0 g |

We concentrated on enhancing the survival of the more fastidious micro-organisms—*Neisseria gonorrhoeae*, *Neisseria meningitidis* and *Haemophilus influenzae*. We also examined the survival of the six test organisms: Salmonella sp., *Streptococcus pyogenes*, Vibrio sp., Shigella sp., *Corynebacterium diphtheriae* and Proteus sp. in various media.

Further modifications of medium No. 6 were based on various factors, which may influence bacterial survival.

EXAMPLE PREPARATION AND USE OF MODIFIED TRANSPORT MEDIUM 26C

Formula:

| | |
|---|---|
| Distilled water | 1000 ml |
| Purified agar | 3.0 g |
| NaCl | 10.0 g |
| KCl | 0.2 g |
| $K_2HPO_4$ | 1.39 g |
| $KH_2PO_4$ | 0.2 g |
| $MgCl_2.6H_2O$ | 10.17 g (50 mM) |
| $CaCl_2.2H_2O$, 1.0% solution | 10.0 ml (0.7 mM) |
| Activated Charcoal Powder | 10.0 g |

1. Heat the agar and the distilled water to dissolve the agar. Remove from heat and cool to about 60° C. before adding the remaining chemicals in order with constant stirring. Add the calcium chloride solution gradually while stirring to prevent precipitation. The medium may be slightly cloudy before the charcoal is added.

2. Dispense in 5.0 ml aliquots in screw cap specimen vials.
3. Autoclave for 20 minutes at 121° C.
4. Invert the vials occasionally as the medium cools in order to distribute the charcoal uniformly.
5. Store the vials at 4° C., but warm them to room temperature before using.
6. On sampling day add 100 µl filter sterilized sodium thioglycolate (0.5 g/10 ml distilled water) to each vial and mix before adding the specimen.
7. If the specimens are to be frozen, add 0.5 ml dimethyl sulfoxide to 4.5 ml medium, or 1.0 ml sterile glycerol to 4.0 ml medium.

RESULTS AND CONCLUSIONS

1. Membrane Stabilization by $Mg^{++}$

In an effort to enhance survival of the more fragile bacteria in transport medium, the divalent Mg cation concentration was adjusted in the basic No. 6 medium. Medium No. 26b (10 mM $Mg^{++}$), No. 26d (25 mM $Mg^{++}$) and No. 26c (50 mM $Mg^{++}$) were examined.

*N. gonorrhoeae* and *N. meningitidis* survived best in No. 26c (50 mM $Mg^{++}$) and remained viable until at least Day 3. There was an increase in survival of these bacteria in No. 26c over both No. 6 and Amies media, expecially for gonococci which previously had not survived 24 hours. *H. influenzae* survived as well in No. 26d as in No. 26c; the survival was not significantly different from that in No. 6 or Amies. The above results are illustrated in FIGS. 1, 2 and 3.

With regard to the standard test organisms, both *C. diphtheriae* and *S. pyogenes* survived better at 20° C. in No. 26c than in No. 6 or Amies. Salmonella, Shigella, Vibrio and Proteus sp. exhibited the common overgrowth phenomenon at 20° C. At 4° C., Salmonella and Shigella showed similar survival in No. 26c. No. 6 and Amies; *C. diphtheriae* and Proteus showed similar survival in No. 6 and No. 26c, which was better than survival in Amies. Vibrio survived best in No. 26c at 4° C., and *S. pyogenes* showed similar survival in Amies and No. 26c. Although *S. pyogenes* survival in No. 26c was lower than that in No. 6, an acceptable survival (25%—Day 14) was achieved in No. 26c.

These results suggest that the inclusion of 50 mM $Mg^{++}$ in No. 6 medium is an important modification, which often enhances the survival of the bacteria tested.

2. Redox Potential

A redox-combination electrode has enabled the study of the oxidation potential of the various media, all of which contain sodium thioglycollate as the reducing agent. It has been found that the initial redox potential of the medium increases with time from an average −100 mV to greater than 180 mV in some cases after an extended storage period at 4° C.

Since a low redox is thought to be essential for the survival of micro-organisms, the survival results obtained would be directly related to the length of storage of the medium prior to testing. This may explain the variations in the following results, especially at 20° C.

| Prep Date | Test Date | % Survival of *H. influenzae* in Amies | | | | | | | | | |
|---|---|---|---|---|---|---|---|---|---|---|---|
| | | Day 0 | | Day 1 | | Day 2 | | Day 3 | | Day 6 | |
| | | 4° | 20° | 4° | 20° | 4° | 20° | 4° | 20° | 4° | 20° |
| 4.9.79 | 8.9.79 | 100 | 100 | 62 | 3 | 45 | 0 | 28 | 0 | <1 | 0 |
| 26.11.79 | 27.11.79 | 100 | 100 | 108 | 85 | 83 | 42 | 39 | 8 | 0 | 0 |
| 26.11.79 | 11.12.79 | 100 | 100 | 79 | <1 | 49 | 0 | 27 | 0 | | |

Storage temperature (4° or 20°) seems to have no significant effect on the change in redox potential. Thus, media stored at 4° or 20° for 6 days and measured on the 7th day showed the following:

| MEDIUM | REDOX POTENTIAL | |
|---|---|---|
| | 20° | 4° |
| No. 6 | 130 mV | 120 mV |
| No. 26c | 120 mV | 110 mV |

All media (except Amies) presently being tested are prepared without reducing agent. On the day of testing 100 µl sterile sodium thioglycollate solution (0.5 g/10 ml distilled $H_2O$) is added per transport vial containing 5 ml medium (0.1% final conc.). The contents are mixed and the vial is inoculated with the test organism, mixed again and sampled.

FIG. 1 shows the redox potential of medium No. 26c following the addition of reducing agent. To vial 1 an additional 100 µl was added after 1 hour. The lower redox potential of vial 1 suggests a possible increase in the routine concentration of sodium thioglycollate used (0.1%). However, Amies (1967) cautions that the recommended concentration of 0.1% should not be exceeded, because thioglycollic acid in higher concentration (1.0%) has pronounced bactericidal properties.

A comparison was made of survival in medium No. 26c in which reducing agent was added on the day of inoculation (No. 26c+) versus time of preparation (No. 26c). The experiment was repeated 2 weeks later. The results for meningococci and gonococci are shown in FIGS. 2 and 3. In both cases decreased survival is seen in medium No. 26c stored 2 weeks (note change in redox). In No. 26c+, although a decrease in survival is seen during the second run, better survival is achieved than in medium with reducing agent added at time of preparation.

Various strains of gonococci were tested in medium No. 26c and No. 26c+

| *N. gonorrhoeae* | % Survival | | | | | | | | | |
|---|---|---|---|---|---|---|---|---|---|---|
| | Day 0 | | Day 1 | | Day 2 | | Day 3 | | Day 6 | |
| | 4° | 20° | 4° | 20° | 4° | 20° | 4° | 20° | 4° | 20° |
| strain 1:26c | 100 | 100 | 68 | 34 | 21 | 7 | 12 | 1 | <1 | |
| :26c+ | 100 | 100 | 37 | 13 | 7 | 1 | 3 | 0 | 0 | |
| strain 4:26c | 100 | 100 | 3 | <1 | <1 | 0 | 0 | | | |
| :26c+ | 100 | 100 | 12 | <1 | 3 | 0 | 1 | | | |
| strain 5:26c | 100 | 100 | 14 | 2 | 2 | 0 | <1 | | | |
| :26c+ | 100 | 100 | 2 | 0 | 0 | 0 | | | | |
| strain 6:26c | 100 | 100 | 17 | 5 | 2 | 0 | 1 | | | |
| :26c+ | 100 | 100 | 46 | 8 | 7 | 2 | 1 | | | |

Survival varies with different strains. All strains tested, however, survive at least 24 hours in medium No. 26c(+) at both 4° and 20°.

Reducing agents, sodium thioglycollate, dithiothreitol and L-(+)-cysteine-HCl, were next compared in medium No. 26c. At 0.1% final concentration dithiothreitol has a lower redox potential than either sodium thioglycollate or cysteine-HCl. The latter two reagents have similar redox potentials. In all cases the redox potential increases with time in uninoculated vials.

Survival curves yielded the following: *Neisseria gonorrhoeae* survived best in No. 26c-sodium thioglycollate; *Haemophilus influenzae* survived best in No. 26c-dithiothreitol; and *Neisseria meningitidis* survived only slightly better in No. 26c-cysteine-HCl.

Dithiothreitol is much more expensive than either sodium thioglycollate or cysteine-HCl and will not be used routinely as the reducing agent. We will continue to use sodium thioglycollate as little difference in survival is obtained with cysteine-HCl.

We are presently comparing survival of the three fastidious microorganisms in the No. 26c medium stored aerobically or anaerobically at 4° and 20° C. It was thought that anaerobic storage may keep reduced medium at a lower redox potential for longer periods of time and hence increase survival of micro-organisms. Initial results showed similar increases in redox potential independent of method of storage. In addition, survival in vials stored anaerobically or aerobically was very similar. It has also been found that the low redox potential can be maintained by storing the transport media in sealed containers under nitrogen atmosphere or under anaerobic conditions.

3. Detoxification

Previous attempts to replace charcoal with other detoxifying agents were unsuccessful. Two other agents dextran (No. 34) and starch (No. 35) were used as detoxifying agents replacing the charcoal in No. 26c (50 mM $Mg^{++}$). Neither medium was successful for the fastidious organisms—with zero or 1% survival on Day 1 for all 3 organisms in No. 34, and zero and 2% survival of N. meningitidis and H. influenzae respectively on Day 1 in No. 35. N. gonorrhoaeae, although 13% survival at 4°, Day 1 in No. 35 showed zero survival at 20° C. in No. 35 and no detectable survival by Day 3 at 4° C.

The 6 test organisms are currently being tested in No. 34 and initial results suggest that dextran is better than silica gel and latex beads, but not as good as bentonite. Dextran however, unlike bentonite, does not form a precipitate which interferes with plate counts. *C. diphtheriae* showed less than 1% survival by Day 4 at 20° C.; Vibrio showed no survival by Day 4 at 4° C. in No. 34. Confluent growth was exhibited by Salmonella, Vibrio and Proteus by Day 4 and Shigella by Day 7.

In an effort to improve the aesthetic quality of the transport medium the charcoal concentration was reduced. *H. influenzae*, *N. gonorrhoeae*, and *N. meningitidis* were tested in No. 26c containing various charcoal concentrations (1.0, 0.75, 0.5, 0.25, 0.1%). FIG. 4 illustrates the results obtained for *H. influenzae*. Survival is similar from 0.5–1.0% charcoal at 4° C. *N. gonorrhoeae* survives best in 1.0% charcoal, survival decreases as charcoal concentration decreases. *N. meningitidis* survives similarly in 0.75 and 1.0% charcoal with survival decreasing as charcoal concentration decreases.

Since 0.5% charcoal yielded comparatively good survival in each case, the reduced charcoal concentration was used to test the six test organisms -Salmonella, *Shigella*, *Proteus* and *Vibrio* species, and *S. pyogenes*, *C. diphtheriae*, in an effort to reduce growth at 20° C. However, the reduced charcoal concentration did not control the growth of Salmonella, Shigella, Proteus and Vibrio species. The reduced charcoal concentration did not affect survival at 4° C. for any of the test organisms.

4. Survival With Freezing

It was determined that survival of *Neisseria meningitidis*, *Neisseria gonorrhoeae* and *Hemophilus influenzae* occurred in 26C supplemented with 20% glycerol or 10% dimethyl sulfoxide. Specimens of Hemophilus influenzae showed excellent survival in both 26C and glycerol or 26C and DMSO for up to two months. At 6 months survival in 20% glycerol and 26C was about 50% and that in 26C plus DMSO was 25%.

*Neisseria gonorrhoeae* demonstrated about 10% survival at 14 days in both media, approximately 5% survival at 21 days and about 5% survival at 2 months in both media. There was no survival at 6 months. *Neisseria meningitidis* demonstrated about 20% survival at 21 days and about 10% survival at 2 months in both media. Survival of 2 to 10% of organisms in 20% of glycerol occurred at 6 months but there was no survival in the DMSO medium. Thus, it was concluded that 20% glycerol in 26C was the better medium for preserving frozen organisms and appears to be an excellent medium for all 3 of the fastidious organisms as well as most of the other organisms which were tested less vigorously.

5. pH Control

The pH of the medium should be kept in a range of 6.5 to 6.9. A pH much above 7 increases the rate of death, particularly of some of the fastidious organisms.

6. Mg Ion Concentration

The concentrations provided for magnesium ion are based upon the compound $MgCl_2.6H_2O$. Based upon atomic weights, magnesium ions represent only a fraction of the total (i.e. 24/203). Thus, in medium 26c, 10.17 g of $MgCl_2.6H_2O$ contains $24/203 \times 10.17 = 1.2$ g Mg ions. This is also equivalent to a concentration of 50 mM. Further, a range from 0.6 to 1.2 grams per liter is equivalent to the concentration range of 25 mM to 50 mM, specified above. Specifically, the concentration of Mg ions in medium 26c is expressed as 50 mM or as 1.2 g/l. Similarly the concentration of Mg ions in medium 26d is 25 mM or 0.6 g/l.

The embodiments of the invention in which an exclusive property or privilege is claimed are defined as follows:

1. A transport medium for microorganisms, which comprises

| | |
|---|---|
| Agar (purified) | 3–4 g |
| NaCl | 10 g |
| KCl | 0.2 g |
| $K_2HPO_4$ | 1.39 g |
| $KH_2PO_4$ | 0.2 g |
| $CaCl_2.2H_2O$ | 0.1 g |
| $Mg^{++}$ | 0.6–1.2 g |
| Activated Charcoal | 5–10 g | and distilled water to a final volume of 1 liter.

2. A transport medium according to claim 1, which comprises about 1.0 g of $Mg^{++}$ per liter of transport medium.

3. A transport medium according to claim 2, which further comprises 10 g of activated charcoal per liter of transport medium.

4. A transport medium according to claim 1, which further comprises about 0.1% sodium thioglycollate.

5. A transport medium according to claim 1, which further comprises about 20% glycerol.

6. A transport medium according to claim 1, wherein the pH of the medium is in the range of 6.5–6.9.

7. A transport medium for micro-organisms, which comprises

| | |
|---|---|
| Agar | 3 g |
| NaCl | 10 g |
| KCl | 0.2 g |
| $K_2HPO_4$ | 1.39 g |
| $KH_2PO_4$ | 0.2 g |
| $CaCl_2.2H_2O$ | 0.1 g |
| $MgCl_2.6H_2O$ | 10.17 g |
| Activated Charcoal | 10 g | and water to a final volume of 1 liter.

8. A transport medium according to claim 7, which further comprises about 0.1% sodium thioglycollate.

9. A transport medium according to claim 7, which further comprises about 20% glycerol.

10. A transport medium according to claim 7, wherein the pH of the medium is in the range of 6.5–6.9.

* * * * *